United States Patent [19]

Storey et al.

[11] 4,202,760
[45] May 13, 1980

[54] APPARATUS AND METHOD FOR PREPARATION OF A HEMODIALYSIS SOLUTION OPTIONALLY CONTAINING BICARBONATE

[75] Inventors: L. Robert Storey, Hollywood, Fla.; Robert C. Hall, Pleasant Hill, Calif.

[73] Assignee: Cordis Dow Corp., Miami, Fla.

[21] Appl. No.: 927,322

[22] Filed: Jul. 24, 1978

[51] Int. Cl.² ............... B01D 13/00; B01D 31/00
[52] U.S. Cl. ............... 210/22 A; 210/96.2; 210/101; 210/321 B; 137/101.11; 222/63
[58] Field of Search ............... 210/321 B, 321 A, 22, 210/101, 188, 194, 96 M; 137/101.11, 90, 93; 128/DIG. 3; 222/193, 63, 61, 129.2

[56] References Cited

U.S. PATENT DOCUMENTS

| | | | |
|---|---|---|---|
| 3,406,826 | 10/1968 | Willock | 210/321 B |
| 3,515,275 | 6/1970 | Bowman | 210/22 |
| 3,528,550 | 9/1970 | Cappelen, Jr. | 210/321 B |
| 3,563,381 | 2/1971 | Edelson | 210/96 |
| 3,579,441 | 5/1971 | Brown | 210/321 B |
| 3,598,727 | 8/1971 | Willock | 210/321 B |
| 3,753,493 | 8/1973 | Mellor | 210/321 B |
| 3,756,473 | 9/1973 | Donahue, Jr. | 222/129.2 |
| 3,847,809 | 11/1974 | Kopf | 210/22 |
| 3,920,556 | 11/1975 | Bowman | 210/321 B |
| 3,927,981 | 12/1975 | Viannay et al. | 23/258.5 |
| 3,962,075 | 6/1976 | Fialkoff et al. | 210/22 A |

OTHER PUBLICATIONS

"Factors In Membrane Design And Selection". . . Trans., Am. Soc. Art. Int. Organs, vol. 14, pp. 36-41, 1968.

Primary Examiner—Charles N. Hart
Assistant Examiner—David R. Sadowski
Attorney, Agent, or Firm—Neal A. Waldrop

[57] ABSTRACT

Apparatus and method for make up of a hemodialysis solution and supply of same to an artificial kidney; the solution optionally contains bicarbonate in any desired amount. The apparatus comprises a recirculation loop which mixes a hemodialysis dialysate concentrate with deaerated water and may include another interconnected recirculation loop adopted to form an aqueous bicarbonate solution. Both recirculation loops mix the concentrates in the recirculation fluid in venturi means operated by continuously controlling the velocity of fluid flowing therethrough to create suction to inject the requisite quantity of concentrate to form the final desired composition in the product hemodialysis solution.

18 Claims, 2 Drawing Figures

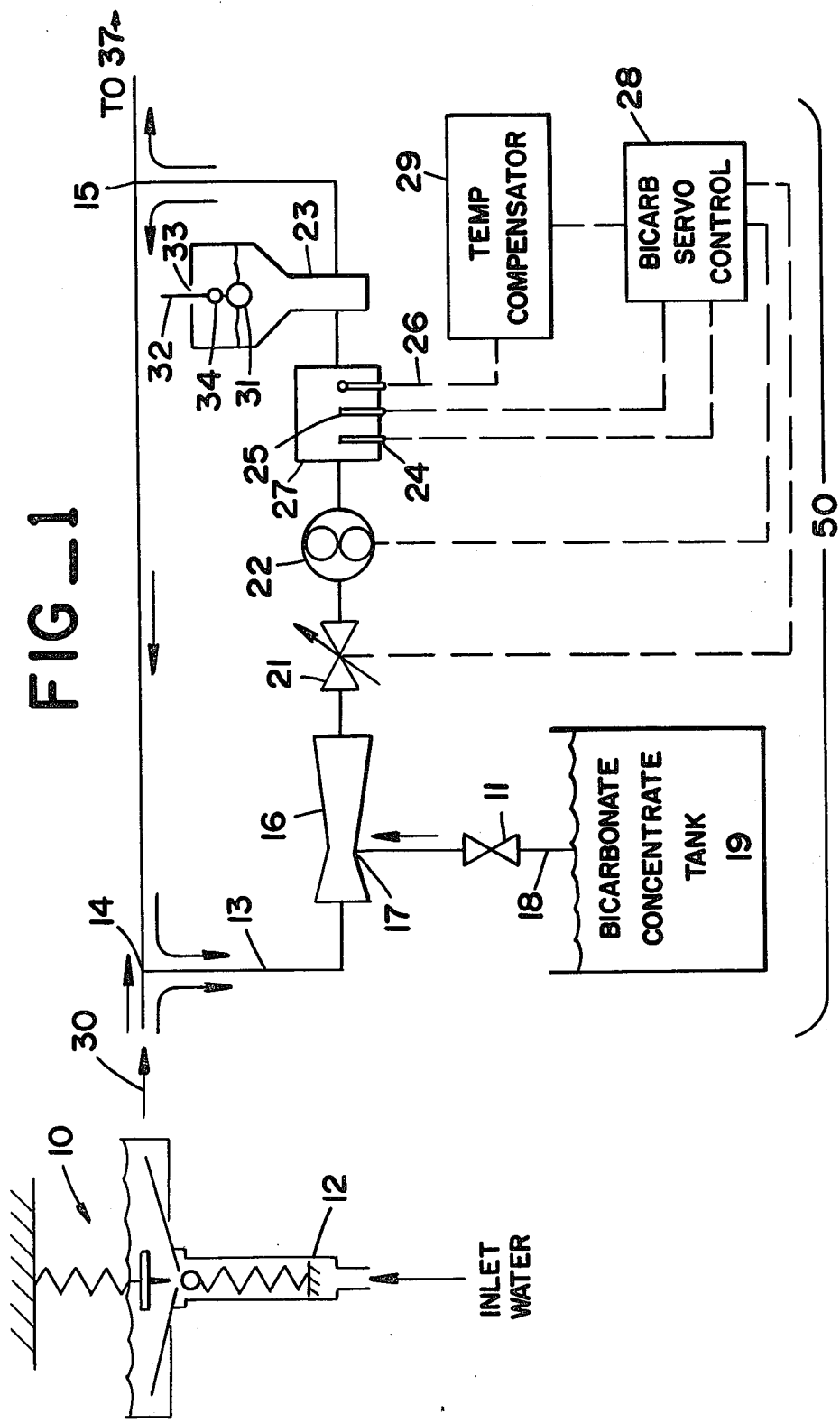

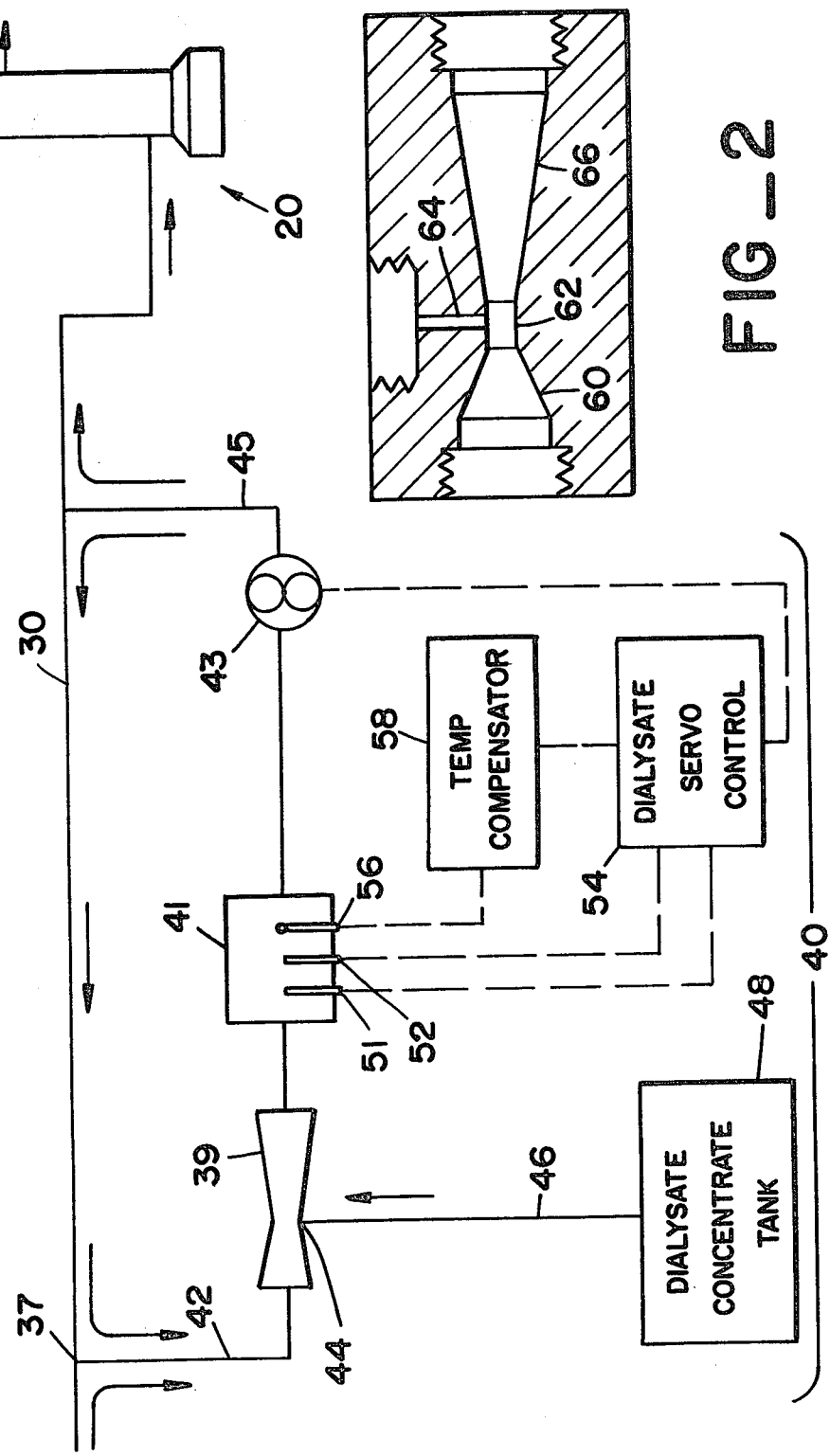

APPARATUS AND METHOD FOR PREPARATION OF A HEMODIALYSIS SOLUTION OPTIONALLY CONTAINING BICARBONATE

BACKGROUND OF THE INVENTION

This invention relates to apparatus and a method of continuously preparing and supplying an optionally bicarbonate-containing hemodialysis solution to an artificial kidney.

Premixed batches of dialysate solution supplied from an open tank by gravity head pressure to a number of artificial kidneys in large clinics have largely been replaced by systems designed to make up and supply dialysate only as needed by each individual artificial kidney. U.S. Pat. Nos. 3,515,275 and 3,920,556 and the several patents identified therein disclose such background prior art and describe the use of positive displacement piston pumps in continuous dialysate supply systems for a single kidney. Other patents which appear to be relevant include U.S. Pat. Nos. 3,406,826, 3,598,727 and 3,878,095; they disclose double acting piston and cylinder units, or variable output positive displacement pumps, which are mechanically adjustable for controllable responsive to measurement of conductivity or dialysate component concentrations to adjust the product solution to preset limits. U.S. Pat. No. 3,847,809 continuously recirculates a dialysate concentrate and at the intersection with the water supply line adds the desired amount of concentrate. In U.S. Pat. No. 2,304,661 a regenerating solution for ion-exchange resins is prepared by mixing acid and water from a measuring tank for the acid previously filled by using the suction created by water flowing through a venturi in the preceding water rinse step. Dialysis concentrate and water are mixed in a venturi device in the direct supply line to a dialysis storage tank in U.S. Pat. No. 3,528,550; additional patents which should be considered to put the present invention in proper perspective with respect to recirculation and venturi use include U.S. Pat. Nos. 3,352,779, 3,690,340, 3,722,680, 3,753,493, 3,843,099 and 3,882,020.

SUMMARY OF THE INVENTION

This invention provides a hemodialysis system which enables continuous formulation and supply to an artificial kidney of a hemodialysis solution, or dialysate, which contains the normally present sodium acetate component, or optionally may contain bicarbonate as a partial or total replacement therefor.

The apparatus comprises a main supply line between a water supply and the kidney and includes a primary recirculation loop including venturi means for mixing the dialysate concentrate with deaerated water and, optionally, a secondary recirculation loop for preliminarily forming a dilute bicarbonate-containing solution which is then fed to the primary recirculation loop for mixing with the other dialysate components and supply to the kidney.

The method requires recirculation of a quantity of the mixed fluid through the mixing venturi in either recirculation loop in an amount which exceeds the fresh water input rate, by an amount of, preferably, 50% to 150% of the fresh water. The preferred operating method includes the bicarbonate addition step as a partial or complete replacement for acetate in the product hemodialysis solution.

GENERAL DESCRIPTION OF THE DRAWINGS

FIG. 1 illustrates the apparatus of this invention in the best known form and arrangement of elements to enable practice of the method disclosed and claimed herein.

FIG. 2 shows a mixing venturi in cross section.

Generally stated, the apparatus consists of a water source, generally designated 10, and a hemodialysis device or artificial kidney generally designated 20 which are interconnected by a main line 30. A dialysate recirculation loop generally designated 40 is located adjacent to the kidney; a bicarbonate recirculation loop generally designated 50 is located adjacent to the water source and both loops are directly connected into main line 30. Dialysate recirculation loop 40 functions to provide normal hemodialysis solution containing acetate whereas the bicarbonate recirculation loop 50 provides a dilute bicarbonate solution which is then fed to downstream loop 40 to be blended, or mixed, with the other dialysate chemical components of normal dialysate concentrate to thereby form the bicarbonate-containing hemodialysis solution of this invention. Loop 50 also contains means for removing dissolved air and bubbles from the incoming water. Each of the recirculation loops 40 and 50, and the method of their use will now be described.

DETAILED DESCRIPTION OF THE INVENTION

As seen in FIG. 1, water enters main line 30 through pressure regulator valve 12, of conventional construction, at a controlled, preselected pressure usually in the range of about 1–10 psi and moves from left to right, toward kidney 20.

The bicarbonate recirculation loop 50 includes a section of main line 30 and a recirculation line 13 which extends from junction 14 at its upstream end to junction 15 at its downstream end. Loop 50 and the elements attached in line 13 provide the dual function of supplying the desired dilute bicarbonate solution and deaeration of the fluid circulating therein. Mixing venturi 16 is located adjacent to junction 14. The throat portion 17 of venturi 16 is connected by line 18 and valve 11 to the pool of aqueous bicarbonate-containing concentrate in tank 19.

The elements for deaerating the circulating fluid consist of variable flow restriction 21, pump 22 and bubble removal means, or air trap 23 which are located downstream of venturi 16, as shown. Conductivity measuring means 27, including probes 24, 25 and a temperature compensation probe 26, all of conventional construction, is located immediately downstream of pump 22; these probes continuously monitor the conductivity of the recirculating fluid which is a mixture of the incoming water and the bicarbonate concentrate from tank 19.

The bicarbonate concentrate may be a simple aqueous bicarbonate solution formulated from sodium bicarbonate and water; other alkali metal carbonates, particularly potassium, are preferably avoided. The preferred concentrate is one which contains a mixture of sodium chloride and sodium bicarbonate with sufficient sodium chloride content to be conductive to a degree that permits accurate determination of small variations from a preset conductivity representing the desired bicarbonate concentration. A concentrate for this purpose may satisfactorily contains 40 g/l to 80 g/l sodium bicarbonate, and 20 g/l to 50 g/l NaCl.

Loop 50 functions to form a dilute aqueous bicarbonate solution and to recirculate same by the pumping action of pump 22, preferably of the gear type. The speed of pump 22 is controlled by, and varies responsive to, control signals from bicarbonate servo-controller 28 functioning in conjunction with temperaure compensator 29; such controls are known and familiar to those skilled in the hemodialysis art and a number of satisfactory units are available commercially in the United States. In accordance with the method of this invention, bicarbonate may replace a portion, or all, of the acetate which is in normal dialysate that is in widespread use in hemodialysis as practiced throughout the world. Loop 50 provides an arrangement whereby any desired strength of aqueous bicarbonate solution may be continuously formulated by first mixing water and concentrate in venturi 16 and then more thoroughly mixing and rendering more uniform the composition of the dilute solution during recirculation in loop 50; the speed of pump 22 has a minimum which produces a velocity of fluid circulation in line 13 that exceeds the rate of flow of incoming water to line 30, we well as the rate of final dialysate flow to kidney 20. Such minimum speed of pump 22 insures recirculation of some quantity of mixed, dilute bicarbonate solution in main line 30 between junctions 15 and 14. It has been found to be desirable to insure that the quantity of mixed fluid recirculating exceeds the quantity of incoming water and is in the range of about 25% to about 300% of that water volume, preferably in the range of about 50% to about 150% of the input water volume.

The momentary speed of pump 22 varies as required to accomplish its multi-functions. The quantity of bicarbonate concentrate which enters the system is dependent on the degree of suction created in the throat 17 of venturi 16 and this suction is directly dependent on the rate of flow of recirculating fluid in line 13; moreover pump 22, venturi 16, and variable restriction valve 21 function to reduce the pressure from the normal input water pressure at 14 of about 1–10 psi downwardly to within the range of 450 to 650 millimeters of mercury negative relative to atmospheric between restriction 21 and pump 22 for the purpose of forming bubbles from the dissolved air in the incoming water so that they may be removed in bubble removing means, or air trap 23. Air trap 23 is satisfactorily of conventional design, and as illustrated includes floating ball 31 carrying stem 32, the vertical movement of which opens or closes air vent 33 as closure 34 seats thereagainst. As above indicated, the speed of pump 22 is increased, or decreased, to create sufficient suction to pull the quantity of bicarbonate concentrate into venturi 16 that after dilution with the incoming water produces the preset conductivity value that is being continuously measured by conductivity unit 27. Typically a small range of conductivity is preset in control 28 and measured variations therefrom cause pump 22 to increase or decrease as needed to maintain the preselected bicarbonate concentration in the dilute solution. Control unit 28 also provides control signals to variable flow restriction 21 to insure sufficient pressure drop in the recirculating fluid to insure bubble formation as the speed of pump 22 varies to maintain the desired bicarbonate concentration. This arrangement of the combination of deaeration and bicarbonate solution formation through the use of a common pump 22, controlled as stated, and their location in a recirculation loop off of main line 30 provides the further advantage that the pressure established by inlet pressure regulator valve 12 extends through junction 14 beyond, and downstream to junction 15, and this constancy of inlet and outlet pressure to loop 50 tends to offset any tendency of pump 22 to undesirably affect the balance of the system due to fluctuations in speed in response to control signals or bubbles of air passing therethrough.

The deaerated dilute bicarbonate-containing solution exits at junction 15 from loop 50 into main line 30 and enters loop 40 at junction 37. Recirculation loop 40 includes, in downstream toward the kidney order, dialysate venturi 39, conductivity measuring unit 41 and pump 43. Venturi 39 is connected at each end into recirculation line 42. The throat 44 of venturi 39 is connected by line 46 to dialysate concentrate tank 48. Conductivity unit 41 is similar to the corresponding unit 27 in loop 50 and includes probes 51, 52 connected to dialysate servo control unit 54, and temperature compensation probe 56, which is connected to temperature compensator control 58 that is, in turn, interconnected with dialysate control 54. Control signals are fed from dialysate servo control 54 to pump 43, which is satisfactorily of the gear or positive displacement type, as in loop 50.

The elements in loop 50 are in operation at all times that a product dialysate is being supplied to kidney 20 except that bicarbonate concentrate tank 19 is inoperative to supply bicarbonate to the throat of venturi 16 when no bicarbonate is desired in the product dialysate. During such time, valve 11 is closed and incoming water passes through line 13, venturi 16, variable flow restriction 21, pump 22 and air trap 23 to thereby remove dissolved air and bubbles therefrom and thus provide a deaerated stream of water to 37 for circulation in dialysate loop 40. It is only necessary to slightly adjust the setting of variable restriction 21 and pump 22 for zero bicarbonate input by appropriate adjustment of bicarbonate servo control 28.

Dialysate venturi 39 and bicarbonate venturi 16 are similar in construction and may best be seen in FIG. 2. The venturi illustrated in FIG. 2 is of the type having a short lead in section 60, an elongated throat portion 62 into the downstream end portion of which concentrate supply line 64 is attached. The downstream or exit end portion 66 is angled much less severely than section 60. The lead in angle, exit angle, throat diameter and overall length of venturis 16 and 39 were selected to maximize suction in throat portion 62 at minimum pressure drop across the venturi for any selected fluid velocity therethrough. Venturis of this general type are commercially available and satisfactory performance has been obtained with a standard Herschel-type venturi.

Dialysate recirculation loop 40 functions on a continuous basis to formulate dialysate solution having the preselected composition and to supply same from pump 43 to main line 30 through line 45, and thence to kidney 20. Pump 43 is controlled similarly to the control of pump 22 in loop 50, as above explained. The amount of recirculation of the mixture of the stream from loop 50 and the fluid formulated in loop 50 which joins that stream at junction 37 should be a quantity which exceeds the incoming stream by an amount in the range of about 25% to about 300% and preferably between about 50% and 150%.

The desired final formulation of dialysate is obtained, and maintained substantially constant by preselecting the small range of conductivity values which correspond to the desired, preselected concentration of bicarbonate and acetate in the otherwise normal dialysate solution.

As used in this specification and in the claims the expression "normal dialysate" refers to the dilute solution which circulates in the artificial kidney on one side of the dialysis membrane and has the following range of composition:
Sodium: 120–150 milliequivalents/liter
Chloride: 90–110 milliequivalents/liter
Calcium: 1–4 milliequivalents/liter
Magnesium: 0–2 milliequivalents/liter
Potassium: 0–3 milliequivalents/liter
Acetate: 30–50 milliequivalents/liter
Dextrose (D-glucose): 0–4 grams/liter Using a selected bicarbonate-saline concentrate within the ranges stated above, conductivity measurements are experimentally determined as a function of bicarbonate concentration in dilute solutions thereof and used for controlling limits for bicarbonate servo control 28. In order to arrive at the appropriate sodium concentration in the final dialysate it is necessary to provide a dialysate concentrate for tank 48 which contains less than the normal amount of sodium and chloride to accommodate the quantities of those ions which are added in the bicarbonate-saline solution product from loop 50 which becomes the input fluid to loop 40 at junction 37. A suitable dialysate concentrate for use in tank 48 may have the following composition:
Sodium Chloride: 100–200 grams per liter
Potassium Chloride: 0.5–7.0 grams per liter
Calcium Chloride: 3–10 grams per liter
Magnesium Chloride: 0.5–8.0 grams per liter
Hydrochloric Acid: 0–8.4 grams per liter
Sodium Acetate: 0–140 grams per liter
Dextrose (D-glucose): 0–135 grams per liter The method of this invention, and the apparatus in loops 50 and 40, provide a spectrum of bicarbonate-acetate containing hemodialysis solutions ranging from no bicarbonate to no acetate. It is to be understood however that all of the dialysate components in the improved hemodialysis solutions of this invention that are present in normal dialysate as above defined, other than acetate, must be present. Moreover where bicarbonate replaces acetate, improvement in patient acceptance occurs in those patients who exhibit some degree of inability to metabolize acetate; where acetate is reduced by as must as about one-fourth of concentration of acetate in normal dialysate, and substituted by bicarbonate, substantial relief from effects approaching morbidity can be realized. Further substitution of bicarbonate for acetate, to and including total substitution is available for election and use by the physician in appropriate cases. Where the concentration of acetate is only reduced, formulations of dialysate concentrates containing lower concentrations of acetate should be substituted in tank 48 to thereby obtain the desired blend of acetate and bicarbonate.

Blends of acetate and bicarbonate offer in combination of advantageous characteristics which include avoidance of undesirable precipitation problems with magnesium or calcium in bicarbonate concentrates and the concurrent ability to avoid undesirable effects with certain patients. The final product hemodialysis solution of this invention is one having a composition as follows:
Sodium ion: 120–150 milliequivalents/liter
Potassium ion: 0–3 milliequivalents/liter
Calcium ion: 1–4 milliequivalents/liter
Magnesium ion: 0–2 milliequivalents/liter
Bicarbonate ion: 0–40 milliequivalents/liter
Chloride ion: 90–110 milliequivalents/liter
Acetate ion: 45–0 milliequivalents/liter
Dextrose (D-glucose): 0–4 grams/liter The following example is set forth to illustrate the best form of the invention presently contemplated for use in hemodialysis where all of the acetate in normal dialysate is replaced by bicarbonate. The hemodialysis solution contains in milli equivalents per liter: $Na^+-137$; $K^+-2$; $Ca^+-3$; $Mg^{+2}-1.5$; $HCO_3^--36$; $Cl^--107.5$. This solution was obtained by using as the bicarbonate-saline concentrate a mixture of 31.4 g/l of NaCl and 60.6 gm/l of $NaHCO_3$ and a modified dialysate concentrate containing 160 gm/l NaCl, 5.5 gm/l KCl, 8.2 g/l $CaCl_2$, 5.6 gm/l $MgCl_2$ and 5.1 gm/l HCl.

As will be readily apparent to those of ordinary skill in this art, hemodialysis solutions having a selected blend of acetate and bicarbonate may be formulated by the routine steps of initial selection of the desired proportions of bicarbonate and acetate, and employed the applicable conductivity values in controllers 28 and 54, together with modifications of the concentrates for tanks 19 and 48; these steps required only routine application of engineering procedures after a few experimental conductivity tests are completed on selected modified concentrates.

What is claimed is:

1. Apparatus for preparing dialysate for use in hemodialysis which comprises a main line connected at its inlet end to a water source and at its exit end to an artificial kidney, a dialysate recirculation line connected into said main line at an upstream end and at a spaced downstream end, and including dialysate venturi means connected at its ends into said recirculation line and at its throat portion with a line to a dialysate concentrate tank, conductivity measuring means in said recirculation line adjacent to and downstream of said venturi means, and pump means in said recirculation line downstream of said conductivity measuring means.

2. Apparatus in accordance with claim 1 wherein the speed of said pump means varies in response to variations in the conductivity of said dialysate from a preselected conductivity value.

3. Apparatus in accordance with claim 1 wherein said conductivity means includes temperature compensating means.

4. Apparatus in accordance with claim 1 wherein a bicarbonate recirculation line is interposed between said water source and the upstream end of said dialysate recirculation line, said bicarbonate line comprising bicarbonate venturi means connected at its ends into said bicarbonate line and at its throat portion to a bicarbonate-saline concentrate tank, pump means in said bicarbonate line downstream of said bicarbonate venturi means, and conductivity measuring means in said bicarbonate line downstream of said pump means.

5. Apparatus in accordance with claim 1 wherein a bicarbonate recirculation line is interposed between said water source and the upstream end of said dialysate recirculation line, said bicarbonate line comprising bicarbonate venturi means connected at its ends into said bicarbonate line and at its throat portion to a bicarbonate-saline concentrate tank, a variable flow restriction downstream of and adjacent to the exit side of said bicarbonate venturi, pump means downstream of and adjacent to said variable flow restriction, conductivity measuring means downstream of and adjacent to said pump means, and bubble removal means downstream of and adjacent to said conductivity measuring means.

6. Apparatus for preparing dialysate for use in hemodialysis which comprises a main line connected at its inlet end to a water source and at its exit end to an artificial kidney, a dialysate recirculation line connected into said main line at an upstream end and at a spaced downstream end, and including dialysate venturi means connected at its ends into said recirculation line and at its throat portion with a line to a dialysate concentrate tank, conductivity measuring means in said recirculation line adjacent to and downstream of said venturi means, pump means in said recirculation line downstream of said conductivity measuring means, and a bicarbonate recirculation line interposed between said water source and the upstream end of said dialysate recirculation line, said bicarbonate line comprising bicarbonate venturi means connected at its ends into said bicarbonate line and at its throat portion to a bicarbonate-saline concentrate tank, pump means in said bicarbonate line downstream of said bicarbonate venturi means, and conductivity measuring means in said bicarbonate line downstream of said pump means.

7. Apparatus in accordance with claim 6 wherein the speed of said pump means in said bicarbonate line varies in response to variations in conductivity of said bicarbonate solution from a preselected conductivity value.

8. Apparatus in accordance with claim 6 wherein said conductivity measuring means includes temperature compensating means.

9. A method for continuously formulating dialysate and supplying same to an artificial kidney which comprises the steps of:
(1) establishing a main line between a water supply and an artificial kidney having a recirculation loop therein provided with dialysate venturi means, recirculation pump means and conductivity measuring means,
(2) establishing a water flow in said main line toward said kidney and removing dissolved air and bubbles to form a deaerated stream,
(3) establishing sufficient suction in the throat of said venturi means by recirculation of fluid therethrough to inject dialysate concentrate into said deaerated stream at said throat,
(4) mixing said concentrate with said recirculating fluid in said venturi means and in said recirculation loop, and
(5) said recirculating fluid consisting of a mixture of water and a portion of said dialysate in an amount exceeding the quantity of fresh water fed into said main line by an amount in the range of about 25% to about 300%.

10. A method in accordance with claim 9 wherein said dialysate has the composition of normal dialysate for use in hemodialysis.

11. A method in accordance with claim 9 wherein said dialysate contains sodium acetate in an amount in the range of about 75% to 0% of the sodium acetate concentration in normal dialysate.

12. A method in accordance with claim 9 wherein the suction in said venturi means in step (3) varies responsive to conductivity variations from a preset conductivity range for the desired composition of said dialysate.

13. A method in accordance with claim 9 wherein the quantity of said recirculating fluid is an amount exceeding the quantity of fresh water fed into said main line in the range of about 50% to about 150%.

14. A method for continuously formulating a bicarbonate-containing hemodialysis solution and supplying same to an artificial kidney which comprises the steps of:
(1) establishing a main line between a water supply and an artificial kidney having a dialysate recirculation loop therein provided with dialysate venturi means, recirculation pump means and conductivity measuring means,
(2) establishing a bicarbonate solution recirculation loop in said main line interposed between said dialysate recirculation loop and said water supply, said bicarbonate solution recirculation loop being provided with bicarbonate venturi means, recirculation pump means, conductivity measuring means and air removal means,
(3) establishing a water flow in said main line toward said kidney and into said bicarbonate recirculation loop,
(4) establishing sufficient suction in the throat of said bicarbonate venturi means by recirculation of fluid therethrough to inject bicarbonate concentrate into said fluid at said throat and mixing same therewith to thereby form a deaerated dilute bicarbonate solution,
(5) forwarding said bicarbonate solution to the said dialysate recirculation loop and recirculating a stream of a mixture of said bicarbonate solution and an aqueous solution of other dialysate components through said dialysate venturi means at a velocity to create sufficient suction to inject dialysate concentrate into said stream at the throat of said dialysate venturi means and mixing same therewith in said means and in said dialysate recirculation loop to thereby form bicarbonate-containing hemodialysis solution having the preselected composition,
(6) the portion of said bicarbonate solution recirculating in said bicarbonate recirculation loop exceeding the quantity of fresh water fed into said main line by an amount in the range of about 25% to about 300%, and
(7) the portion of said stream of a mixture of said bicarbonate solution and said bicarbonate-containing hemodialysis solution recirculating in said dialysate recirculation loop exceeding the quantity of bicarbonate solution fed to the upstream end of said dialysate recirculation loop by an amount in the range of about 25% to about 300%.

15. A method in accordance with claim 14 wherein said dialysate contains sodium acetate in an amount in the range of about 75% to 0% of the sodium acetate concentration in normal dialysate.

16. A method in accordance with claim 14 wherein the suction in said venturi means in step (4) varies responsive to conductivity variations from a preset conductivity range for the desired composition of said bicarbonate solution.

17. A method in accordance with claim 14 wherein the suction in the venturi means in step (5) varies responsive to conductivity variations from a preset conductivity range for the desired composition of said hemodialysis solution.

18. A method in accordance with claim 14 wherein the quantity of said recirculating fluids in each of said recirculating loops is an amount in the range of abut 50% to about 150% of the fresh water fed to said main line.

* * * * *